(12) United States Patent
Harrison et al.

(10) Patent No.: US 9,486,275 B2
(45) Date of Patent: Nov. 8, 2016

(54) ELECTROSURGICAL APPARATUS HAVING A SENSOR

(75) Inventors: Robert Harrison, Milton (CA); Neil Godara, Milton (CA); Kathleen Bell, Mississauga (CA); Anton Santhiapillai, Scarborough (CA)

(73) Assignee: Avent, Inc., Alpharetta, GA (US)

( * ) Notice: Subject to any disclaimer, the term of this patent is extended or adjusted under 35 U.S.C. 154(b) by 1320 days.

(21) Appl. No.: 12/981,681

(22) Filed: Dec. 30, 2010

(65) Prior Publication Data
US 2012/0172857 A1 Jul. 5, 2012

(51) Int. Cl.
*A61B 18/14* (2006.01)
*A61B 18/00* (2006.01)

(52) U.S. Cl.
CPC .. *A61B 18/1477* (2013.01); *A61B 2018/00642* (2013.01); *A61B 2018/00702* (2013.01); *A61B 2018/00821* (2013.01); *A61B 2018/00875* (2013.01); *A61B 2090/3966* (2016.02)

(58) Field of Classification Search
CPC ............... A61B 18/1477; A61B 2018/00642; A61B 2018/00821; A61B 2018/1472
USPC ............ 606/33, 41, 42; 604/164.01, 166.01, 604/170.02
See application file for complete search history.

(56) References Cited

U.S. PATENT DOCUMENTS

| | | | |
|---|---|---|---|
| 4,411,266 A | 10/1983 | Cosman | |
| 4,907,589 A | 3/1990 | Cosman | |
| 5,085,659 A * | 2/1992 | Rydell | 606/47 |
| 5,233,515 A | 8/1993 | Cosman | |
| 5,334,193 A | 8/1994 | Nardella | |
| 5,342,383 A * | 8/1994 | Thomas | 606/19 |
| 5,383,874 A | 1/1995 | Jackson et al. | |
| 5,423,811 A | 6/1995 | Imran et al. | |
| 5,458,596 A | 10/1995 | Lax et al. | |
| 5,484,400 A | 1/1996 | Edwards et al. | |
| 5,536,267 A | 7/1996 | Edwards et al. | |
| 5,546,161 A | 8/1996 | Sakai et al. | |
| 5,569,242 A | 10/1996 | Lax et al. | |
| 5,651,780 A | 7/1997 | Jackson et al. | |

(Continued)

FOREIGN PATENT DOCUMENTS

| | | |
|---|---|---|
| EP | 1707149 | 10/2006 |
| WO | WP 99-34860 | 7/1999 |
| WO | WO 2006-096978 | 9/2006 |

OTHER PUBLICATIONS

U.S. Appl. No. 11/280,604, filed Nov. 15, 2005, Godara et al., Methods of Treating the Sacroiliac Region of a Patient's Body.

(Continued)

*Primary Examiner* — Michael Peffley
*Assistant Examiner* — Thomas Giuliani
(74) *Attorney, Agent, or Firm* — Dority & Manning, P.A.

(57) ABSTRACT

An electrosurgical apparatus for treating tissue comprises an elongate shaft including a proximal region, a distal region having an electrically conductive region and one or more lumens through the shaft. A stylet is located within one of the lumens for obturating at least a portion of an opening defined by a distal end of the elongated shaft. The stylet distal end has a sensor and may include an occluding component substantially surrounding and affixed to it. The elongated shaft and the stylet can possibly be configured to allow passage of fluid through the lumen while the stylet is located within the lumen. Related stylet configurations are also disclosed.

7 Claims, 10 Drawing Sheets

(56) References Cited

U.S. PATENT DOCUMENTS

| | | |
|---|---|---|
| 5,658,278 A | 8/1997 | Imran et al. |
| 5,697,927 A | 12/1997 | Imran et al. |
| 5,785,705 A | 7/1998 | Baker |
| 5,971,980 A | 10/1999 | Sherman |
| 6,015,407 A | 1/2000 | Rieb et al. |
| 6,016,809 A | 1/2000 | Mulier et al. |
| 6,035,238 A | 3/2000 | Ingle et al. |
| 6,053,912 A | 4/2000 | Panescu et al. |
| 6,053,937 A | 4/2000 | Edwards et al. |
| 6,074,412 A | 6/2000 | Mikus et al. |
| 6,123,702 A | 9/2000 | Swanson et al. |
| 6,146,380 A | 11/2000 | Racz et al. |
| 6,162,216 A | 12/2000 | Guziak et al. |
| 6,183,468 B1 | 2/2001 | Swanson et al. |
| 6,217,573 B1 | 4/2001 | Webster |
| 6,228,081 B1 | 5/2001 | Goble |
| 6,241,725 B1 | 6/2001 | Cosman |
| 6,264,651 B1 | 7/2001 | Underwood et al. |
| 6,277,112 B1 | 8/2001 | Underwood et al. |
| 6,283,961 B1 | 9/2001 | Underwood et al. |
| 6,293,943 B1 | 9/2001 | Panescu et al. |
| 6,296,636 B1 | 10/2001 | Cheng et al. |
| 6,315,777 B1 | 11/2001 | Comben |
| 6,355,032 B1 | 3/2002 | Hovda et al. |
| 6,416,508 B1 | 7/2002 | Eggers et al. |
| 6,432,103 B1 | 8/2002 | Ellsberry et al. |
| 6,451,015 B1 | 9/2002 | Rittman, III et al. |
| 6,468,270 B1 | 10/2002 | Hovda et al. |
| 6,468,274 B1 | 10/2002 | Alleyne et al. |
| 6,482,204 B1 | 11/2002 | Lax et al. |
| 6,494,880 B1 | 12/2002 | Swanson et al. |
| 6,500,173 B2 | 12/2002 | Underwood et al. |
| 6,557,559 B1 | 5/2003 | Eggers et al. |
| 6,604,003 B2 | 8/2003 | Fredricks et al. |
| 6,620,155 B2 | 9/2003 | Underwood et al. |
| 6,712,811 B2 | 3/2004 | Underwood et al. |
| 6,749,605 B2 | 6/2004 | Ashley et al. |
| 6,767,347 B2 | 7/2004 | Sharkey et al. |
| 6,772,012 B2 | 8/2004 | Ricart et al. |
| 6,837,884 B2 | 1/2005 | Woloszko |
| 6,878,155 B2 | 4/2005 | Sharkey et al. |
| 6,896,675 B2 | 5/2005 | Leung et al. |
| 6,929,640 B1 | 8/2005 | Underwood et al. |
| 7,306,596 B2 * | 12/2007 | Hillier et al. .................. 606/41 |
| 7,309,336 B2 | 12/2007 | Ashley et al. |
| 8,187,268 B2 * | 5/2012 | Godara et al. .................. 606/41 |
| 8,740,925 B2 * | 6/2014 | Bettuchi et al. .............. 606/185 |
| 2002/0019626 A1 | 2/2002 | Sharkey et al. |
| 2002/0032441 A1 | 3/2002 | Ingle et al. |
| 2005/0177209 A1 | 8/2005 | Leung et al. |
| 2005/0234445 A1 | 10/2005 | Conquergood et al. |
| 2006/0224156 A1 | 10/2006 | Arts et al. |
| 2008/0167646 A1 * | 7/2008 | Godara et al. .................. 606/41 |

OTHER PUBLICATIONS

U.S. Appl. No. 11/356,706, filed Feb. 17, 2006, Godara et al., Electrosurgical Device with Discontinuous Flow Density.
International Search Report from PCT/CA2011/050731—5 pages.

* cited by examiner

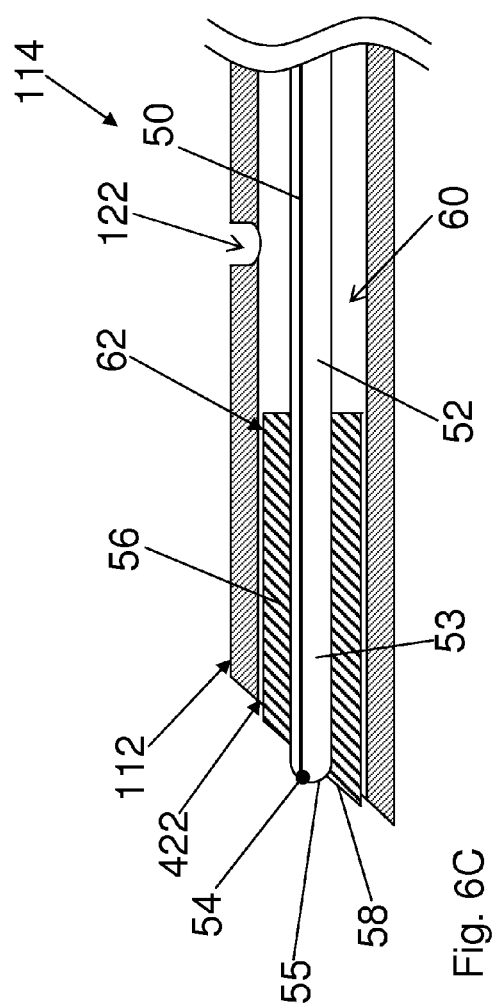
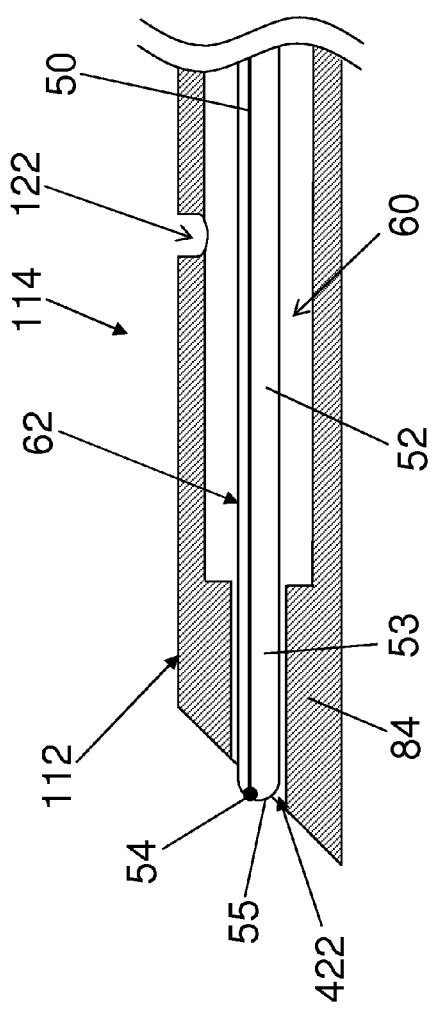
Fig. 6C
Fig. 6D

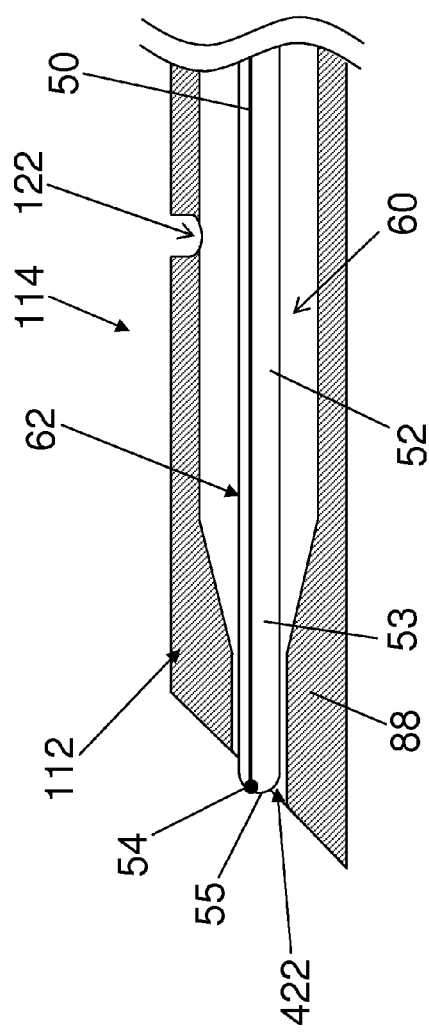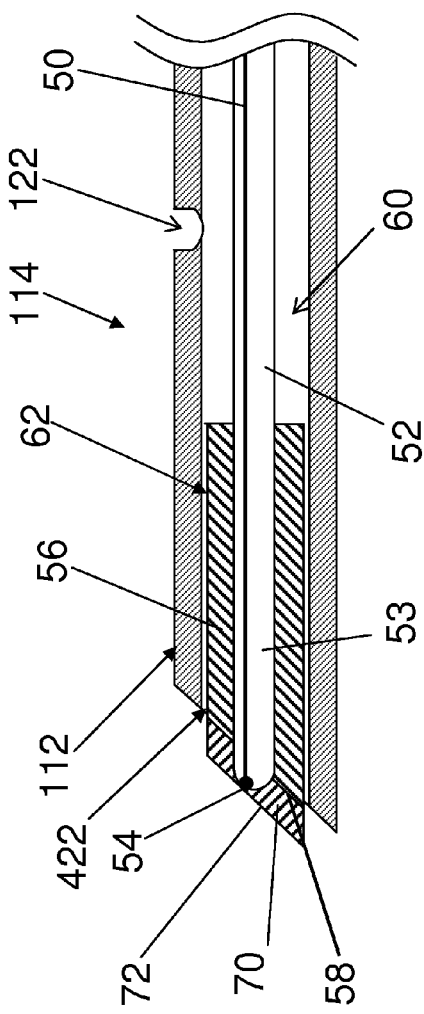
Fig. 6E
Fig. 6F

ELECTROSURGICAL APPARATUS HAVING A SENSOR

TECHNICAL FIELD

The present disclosure relates to electrosurgical devices and more particularly to devices used to deliver high or radio frequency electrical current to a target area in a body and to thermal energy devices used to deliver heat to a target area.

BACKGROUND

Electrosurgical procedures typically rely on the application of high frequency, for example radio frequency (RF), energy to treat, cut, ablate or coagulate tissue structures such as, for example, neural tissue. One example of a treatment procedure incorporating the application of RF energy to treat neural tissue is lumbar facet denervation. The efficacy of the minimally invasive technique of delivering RF electrical current to neural tissue in lumbar facet denervation has been studied at length and these studies show that this procedure is an effective method of relieving low back pain. The high frequency energy is often delivered to a region of tissue from an energy source such as a generator via a probe that is inserted into a patient's body through an introducer needle. The resistance of tissue, located proximate a conductive region of the probe, to the high frequency energy, causes the tissue temperature to rise. The temperature is generally increased to a sufficient level to coagulate unmyelinated nerve structures, at which point a lesion is formed, resulting in pain relief. The probe is typically a stainless steel electrode that is manufactured to fit within an introducer needle (which may also be referred to as a cannula or tube). Some probes incorporate a temperature sensor to allow for monitoring of temperature throughout the procedure. The temperature can be used to control the delivery of the high frequency energy.

Introducer needles with varying geometries are used in such applications. For example, a tip of the introducer needle can be pointed, blunt and rounded, or open, varying in shape in accordance with the needs of different procedures. Pointed tips allow for penetration of tissue without the need for an external device while rounded tips are useful in soft tissue areas such as the brain where it is critical not to damage nerves. An introducer needle typically includes an insulated shaft with an electrically exposed and conductive tip at the distal end of the introducer. A hub at the proximal end of the introducer can also be provided as a connection site for an injection syringe. Introducer needles can therefore be used to inject anesthetic fluid or other treatment compositions, such as therapeutic agents, in addition to playing a role in the insertion of a device into a patient's body and the delivery of electrical energy to a region of tissue.

A typical treatment procedure utilizes an introducer needle having a hollow shaft and a removable stylet therein. This introducer needle is inserted into the patient's body and positioned via imaging technology. Once the introducer needle is positioned, the stylet is withdrawn. The distal end of the probe is then inserted into the shaft of the introducer needle until the distal end of the probe is at least flush with the distal end of the shaft. The probe is connected to a generator that generates electrical current.

Examples of conventional devices include U.S. Pat. No. 6,146,380 to Racz et al., which describes introducer needles with curved conductive tips used in high frequency lesioning procedures. Guziak et al. disclose a medical instrument including a cannula or probe used to penetrate tissue to perform biopsies and RF ablation that may have thermocouple formed at the tip of the probe in U.S. Pat. No. 6,162,216. U.S. Pat. No. 4,411,266 to Cosman is directed to a thermocouple radio frequency lesion electrode with a thermocouple temperature sensor in its distal end.

However, improvement of conventional RF electrosurgical devices to provide more efficient structure and/or surgical procedure, potentially with less trauma for the patient in various aspects would always be welcomed, including devices improving upon one or more o the drawbacks of the conventional devices discussed above.

SUMMARY

According to a first broad aspect of embodiments disclosed herein, an electrosurgical apparatus is provided for treating tissue. The electrosurgical apparatus for treating tissue comprises: an elongated shaft including a proximal region, a distal region having a conductive region, and one or more lumens therethrough; and a stylet located within one of the one or more lumens for obturating at least a portion of an opening defined by a distal end of the elongated shaft to define an obturated portion. The stylet comprises a thermocouple having a thermocouple distal end, with the thermocouple distal end occluding at least part of the obturated portion. Various options and modifications are possible.

For example, some embodiments of the first aspect of the disclosure include an occluding component substantially surrounding and affixed to a distal portion of the thermocouple. Other possible embodiments of the first aspect may include: the obturated portion being at least partially occluded by the occluding component; a wall of the elongated shaft defining one or more apertures in communication with at least one of the one or more lumens; a radiopaque marker extending the length of the occluding component; and the occluding component being comprised substantially of radiopaque material.

Other possible embodiments of the first aspect of the disclosure include: the thermocouple comprising an elongated member having a thermocouple junction formed at a distal end of the elongated member; the occluding component defining a beveled distal face; the thermocouple extending beyond the beveled distal face; and the occluding component comprising a metal.

Other possible features of embodiments of the first aspect of the disclosure include: the opening defined by the distal end of the elongated shaft being sized so that the thermocouple distal end substantially occludes at least a majority of the opening; and optionally a diameter of the distal end opening being less than a diameter of the one of the one or more lumens at a proximal region of the elongated shaft whereby fluid may be injected through the one of the one or more lumens while the thermocouple is occluding the distal end opening. It is possible the diameter of the one of the one or more lumens gradually decreasing towards the distal end opening; and it also possible the diameter of the one of the one or more lumens decreasing at a substantially discrete location along the elongated shaft between the proximal region and the distal end opening of the elongated shaft.

According to a second broad aspect of embodiments of the disclosure, there is provided an electrosurgical apparatus for treating tissue, comprising: an elongated shaft including a proximal region and a distal region having a conductive region, and defining a lumen therethrough. A stylet is located within the lumen having a distal end for obturating at least a portion of an opening defined by a distal end of the elongated shaft to define an obturated portion, with the stylet distal end having a sensor, and the elongated shaft and the stylet being configured to allow passage of fluid through the lumen while the stylet is located within the lumen. Again, various options and modifications are possible.

Some embodiments of the second aspect of the disclosure can include an occluding component substantially surrounds the sensor. Other possible embodiments of the first aspect may include: the obturated portion being at least partially occluded by the occluding component; the sensor comprising a thermocouple junction; the stylet comprising an elongated member having a distal portion including the sensor with an occluding component affixed thereto; the occluding component defining a beveled distal face; the elongated member extending beyond the beveled distal face; and the occluding component comprising a metal with the stylet further comprising a metallic lamina disposed upon at least a portion of the beveled distal face.

Other possible embodiments of the second aspect of the disclosure include: a wall of the elongated shaft defining one or more apertures in communication with the lumen; the apparatus further comprising a radiopaque marker extending the length of the occluding component; and the occluding component being comprised substantially of radiopaque material.

According to other aspects of the disclosure, a stylet is disclosed for use in an electrosurgical apparatus having an elongated shaft including a proximal region, a distal region having a conductive region for RF procedures and a distal opening, and a lumen therethrough. The stylet includes an occluding component sized to obturate at least a portion of the distal opening of the elongated shaft, an elongated member attached to the occluding component and having a distal end, and a thermocouple junction formed at the distal end of the elongated member. The thermocouple provides temperature information during the RF procedures. As above, various options and modifications are possible.

BRIEF DESCRIPTION OF THE DRAWINGS

These and other features of the embodiments of the disclosure will become more apparent in the following detailed description in which reference is made to the appended drawings wherein:

FIGS. 6A-6G are sectional side views through the shaft of exemplary embodiments of the disclosure comprising a stylet with a sensor;

DETAILED DESCRIPTION

Figure 1:
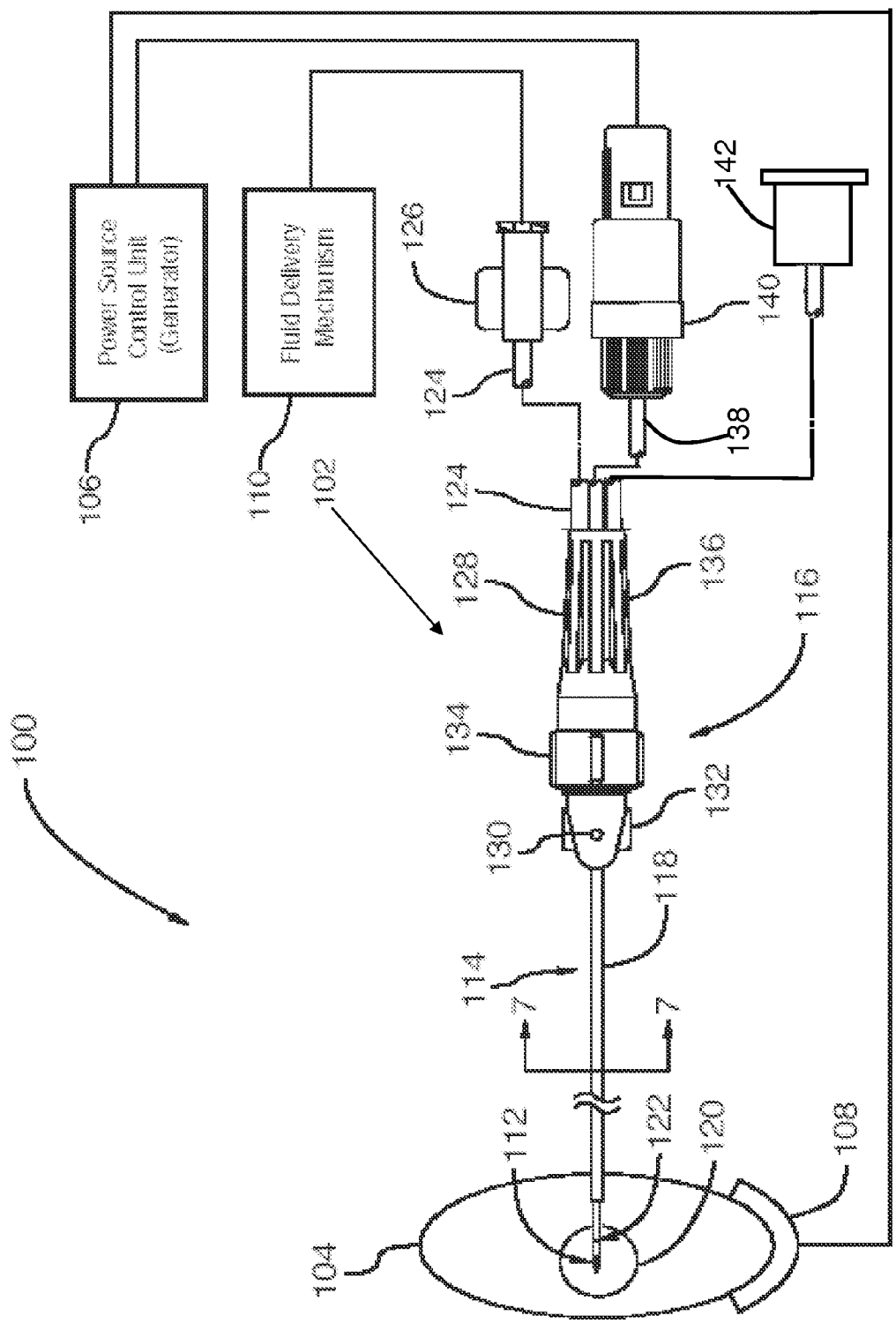
FIG. 1 is a plan elevation view, fragmented, of a system incorporating an electrosurgical apparatus in accordance with a first embodiment of the disclosure.

With specific reference now to the drawings in detail, it is stressed that the particulars shown are by way of example and for purposes of illustrative discussion of certain embodiments of the present disclosure only. In this regard, no attempt is made to show structural details of the apparatus in more detail than is necessary for a fundamental understanding of the embodiments of the disclosure, the description taken with the drawings making apparent to those skilled in the art several forms of the disclosure may be embodiments in practice.

Before explaining embodiments of the disclosure in detail, it is to be understood that the disclosure is not limited in its application to the details of construction and the arrangement of the components set forth in the following description or illustrated in the drawings. The disclosure is capable of other embodiments or of being practiced or carried out in various ways. In some instances, well-known structures and/or processes may not have been described or shown in detail to not obscure the disclosure. Also, it is to be understood that the phraseology and terminology employed herein is for the purpose of description and should not be regarded as limiting.

Referring first to FIG. 1, an electrosurgical apparatus 102 in accordance with an embodiment of the surgical apparatus is shown in a system 100 for treating a body 104. System 100 comprises the electrosurgical apparatus 102; a power source control unit 106; a return dispersive electrode 108; and a fluid delivery mechanism 110, such as, but not limited to, a syringe, for fluid composition injection. Power source control unit 106 may perform at least one of the following functions: supplying energy, for example RF energy, to apparatus 102; measuring temperature feedback from at least one temperature sensor of apparatus 102; and providing impedance measurement between a conductive region 112 of apparatus 102 and return dispersive electrode 108. Impedance measurement may be used during placement to target a body tissue that has specific electrical properties. Apparatus 102 may comprise a conductive shaft 114 and a handle 116. Conductive shaft 114 has an insulating coating 118 along a major portion of its outer surface, terminating adjacent exposed conductive region 112. Conductive region 112 may be operable to transmit energy to a target area 120 of body 104. In addition, conductive region 112 may aid in the penetration of apparatus 102 into body 104 and in the navigation of apparatus 102 to a desired target area 120. It will therefore be understood by a person skilled in the art that conductive region 112 can be of varying dimensions and shapes and may be positioned at various locations on an apparatus 102 of the present disclosure. For example, conductive region 112 can be pointed, sharp, blunt, or open, varying in shape in accordance with the requirements of different procedures. Also, while the length of conductive region 112 in the first embodiment is between about 2 mm to about 10 mm, this length may vary depending on procedural requirements. Conductive region 112 may optionally be made of medical grade stainless steel, but other conductive biocompatible materials may be used as well.

In an embodiment, shaft 114 and conductive region 112 are made from a conductive material, for example, stainless steel. Insulating coating 118 can be made of any type of insulating material, including but not limited to Polyethylene Terepthalate (PET), to prevent shaft 114 from delivering high frequency electrical current to tissue surrounding shaft 114. This coating can be applied using dip coating, heat shrink coating or any other method that would be understood by a person skilled in the art.

Figure 2A:
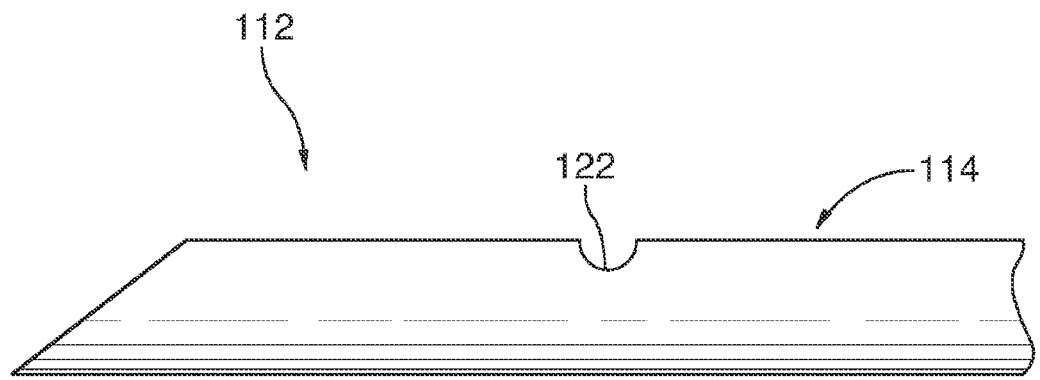
FIGS. 2A-2C are side elevation views of various embodiments of a distal region of an electrosurgical apparatus.
Figure 2B:
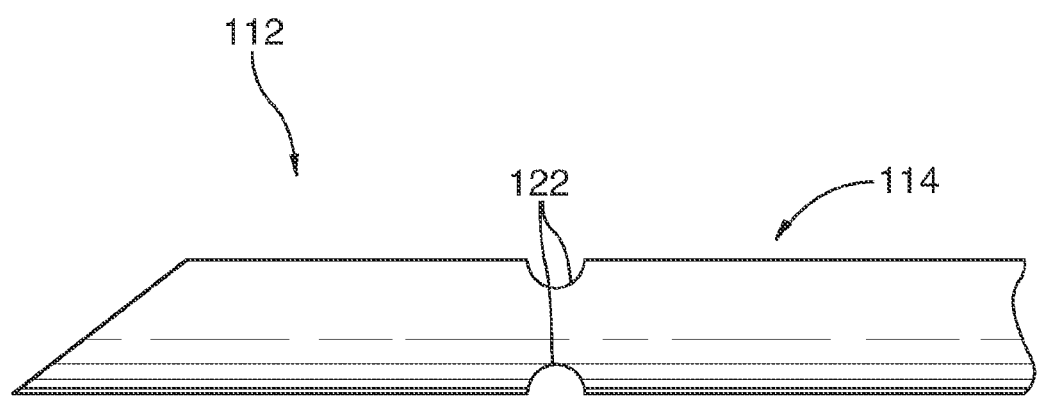
Figure 2C:
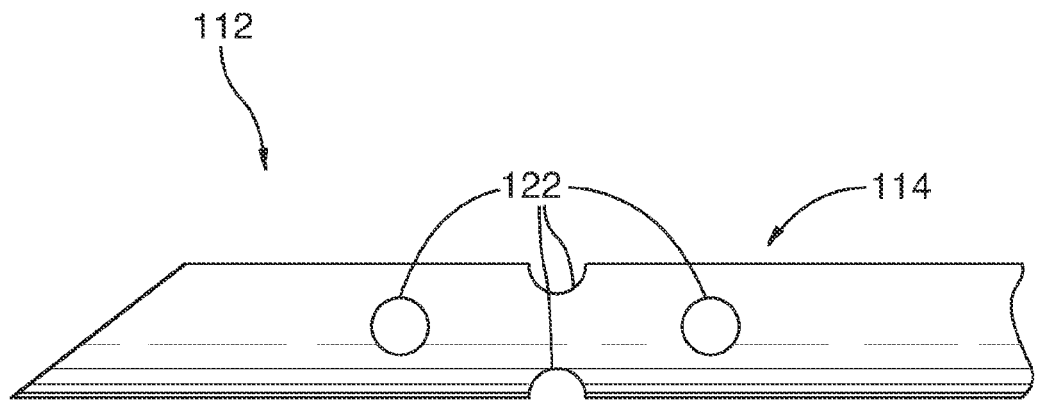

Shaft 114 optionally has at least one aperture 122, through which a treatment composition may exit from apparatus 102. In one embodiment, illustrated in FIG. 2A, aperture 122 is defined by conductive shaft 114 at a side thereof, for example at or proximate conductive region 112. The circumferential edge of aperture 122, on the outer wall of shaft 114, is optionally smooth to prevent cutting of tissue while apparatus 102 is inserted through body 104. In embodiments where aperture 122 is located at or proximate conductive region 112, aperture 122 beneficially allows fluid to be administered to body tissue 104 adjacent conductive region 112. If the treatment composition is electrically conductive, its delivery may provide better conductivity from conductive region 112 to target area 120 surrounding conductive region 112 and greater efficacy of the energy delivered to body tissue 104. A treatment composition may be delivered to a larger area of body tissue surrounding conductive region 112 by rotating apparatus 102 about the axis of conductive shaft 114 while simultaneously administering treatment composition through aperture 122. Furthermore, as shown in FIG. 2B, more than one aperture 122 may be disposed circumferentially around shaft 114 in order to allow for substantially simultaneous delivery of a treatment composition to a larger region of tissue surrounding conductive region 112. Alternatively or in addition, a treatment composition may be delivered to a specific region of tissue by rotating apparatus 102 about the axis of conductive shaft 114 to a desired orientation to target specific body tissue and subsequently administering treatment composition through aperture 122. In other embodiments, aperture 122 may be located at a different region of shaft 114, it may have various shapes and sizes and there may be more than one aperture 122. An exemplary depiction of such an embodiment is shown in FIG. 2C.

Conductive shaft 114 of apparatus 102 may impart rigidity to apparatus 102 to facilitate the maneuvering of conductive region 112 to reach target area 120, in which case shaft 114 may be referred to as being rigid or semi-rigid. In alternate embodiments, shaft 114 may be flexible. In the first embodiment of the disclosure, shaft 114 is hollow along its length, defining a lumen. Shaft 114 may be used to transmit a treatment composition to conductive region 112 and/or target area 120, as well as to support and enclose any wiring associated with apparatus 102. As well, an inner diameter of shaft 114 may be sufficiently dimensioned to accommodate a stylet or obturator in embodiments with an open tip, in addition to wiring for a temperature sensor associated with the distal end of shaft 114. In some embodiments, intended for use in spinal procedures, the length of shaft 114 may vary between about 5 cm to about 15 cm. It is understood, however, that the length may vary beyond this range according to the procedure being performed.

In an embodiment, handle 116 optionally comprises a flexible tube 124 coupled thereto in fluid communication with the lumen of shaft 114. The flexibility of tube 124 may beneficially allow for greater maneuverability of apparatus 102. A proximal end of flexible tube 124 may be coupled to a fluid delivery interface connection 126. In other embodiments of the disclosure (not shown), handle 116 may not be necessary and flexible tube 124 may be coupled directly to shaft 114. Handle 116 also optionally provides a grip 128 to allow a user to manipulate apparatus 102. In one embodiment, handle 116 is manufactured from medical grade injection-moldable plastic or other material that can be sterilized using, for example, ethylene oxide. Handle 116 optionally has an aperture marker 130, in line with aperture 122 along the axis of shaft 114, to indicate the orientation of aperture 122 about the axis of shaft 114. Aperture marker 130 allows the user to target tissue for the delivery of a treatment composition by indicating the orientation of aperture 122. Handle 116 may further comprise orientation markings, including first orientation markings 132 to indicate, for example, a 180° rotation of apparatus 102 about the axis of shaft 114 and second orientation markings 134 to indicate, for example, a 90° rotation of apparatus 102 about the axis of shaft 114. The user may refer to first and/or second orientation markings 132,134 to prevent apparatus 102 from rotating about the axis of shaft 114 while apparatus 102 is inserted through body tissue 104, or to rotate apparatus 102 about the axis of shaft 114 to a desired orientation. First and second orientation markings 132, 134 may be visual indicators, which may be flush with handle 116, or tactile indicators, which may be textured or raised so that the user may see or feel markings 132, 134 as apparatus 102 is inserted into body 104. A proximal end of handle 116 optionally has a strain relief 136 with grip 128 running from the proximal end to the distal end of strain relief 136. In the depicted embodiment, grip 128 is textured, for example with parallel ridges, to provide points of friction for the user while apparatus 102 is rotated about the axis of shaft 114 and inserted through body 104. In this embodiment, the ridges on grip 128 may also be used to determine an angle of rotation of the apparatus. In one embodiment, strain relief 136 has a non-round (non-circular) cross-section, which may be square, triangular, or "toothed" like a mechanical gear. Strain relief 136 may be tapered with a larger distal outer diameter, in order to fit with handle 116, and a smaller proximal outer diameter, in order to secure electrical cable 138 and flexible tubing 124. This taper provides increased grip for the user and reduces slipping of the user's fingers as apparatus 102 is advanced into body 104. Strain relief 136 may provide a comfortable handle for the user and may conform to a user's gripping preference. Strain relief 136 may be, for example, a soft flexible bend relief able to support electrical cable 138 and flexible tubing 124. In the embodiment shown in FIG. 1, electrical cable 138 and flexible tubing 124 extend from handle 116 and strain relief 136 in parallel and adjacent each other. Notably, in this embodiment, electrical cable 138 and flexible tubing 124 do not extend from handle 116 perpendicular to one another. This arrangement can provide a comfortable grasp and can enhance the ease of manipulation of apparatus 102 during placement, rotation, insertion, etc.

Electrical energy may be supplied to conductive region 112 from power source control unit 106 via an electrical coupling, comprising electrical connector 140, electrical cable 138 and conductive shaft 114. All electrical contacts, except for conductive region 112, may be isolated from the user by a connector pin housing located in electrical connector 140. Electrical cable 138 may be flexible for flexibly coupling power source control unit 106 to conductive shaft 114, which supplies energy to conductive region 112. Electrical cable 138 may also relay temperature data back to power source control unit 106. In an embodiment of the disclosure, one conductor in electrical cable 138 acts as both a thermocouple wire as well as an RF delivery wire, as will be described in greater detail below. Utilizing a single conductor for both purposes reduces the overall mass of electrical cable 138 and minimizes the forces and moments applied at handle 116 during placement of apparatus 102 in body tissue 104. It will be understood by a person skilled in the art that separate cables and/or conductors may alternatively be used in conjunction with a temperature sensor.

A fluid delivery mechanism 110 may be flexibly coupled to fluid delivery interface connection 126, and through it to shaft 114 via flexible tubing 124, in order to allow the administration of a treatment composition to a region of tissue in a patient's body. Therefore, as a benefit of the present disclosure, apparatus 102 may be simultaneously connected to fluid delivery mechanism 110 and power source control unit 106 in order to treat body 104. Fluid delivery interface connection 126 may be any connector including, but not limited to, a luer type connector, that allows for the flow of fluid from fluid delivery mechanism 110 to flexible tubing 124.

In operation, apparatus 102 is inserted into body 104 and placed at target location 120. Proper placement of apparatus 102 may be confirmed by applying electrical energy, such as RF energy, using conductive region 112 to stimulate target area 120. An anesthetic fluid or another treatment composition can then be administered by actuating fluid delivery mechanism 110. Apart from pharmacological agents, including anesthetics, the applied treatment composition can include, for example, a fluid that is electrically conductive, a fluid used to heat or cool the tissue or a fluid, such as a dye, that may be used to help visualize a treatment site. The treatment composition exits fluid delivery mechanism 110 and flows through fluid delivery interface connection 126, flexible tube 124, and the lumen of shaft 114 to conductive region 112 where it exits through aperture 122. The incorporation of a fluid delivery system into apparatus 102, as herein described, beneficially allows fluid delivery mechanism 110 to be pre-connected to fluid delivery interface connection 126. Thus, the disclosed apparatus helps to reduce the likelihood of inadvertent movement of conductive region 112 by removing the requirement to use and therefore remove a separate apparatus to apply a treatment composition, which would generally result in an adjustment of the position of conductive region 112. Additionally, the use of flexible tube 124 further decreases the forces acting on handle 116 and shaft 114 when fluid delivery mechanism 110 is actuated to administer the treatment composition, for example, when a plunger on a syringe is depressed. Therefore, after stimulation to confirm proper placement of apparatus 102, manual manipulation of apparatus 102 is minimized and thus the likelihood of shifting apparatus 102, and thus conductive region 112, out of position is decreased. In addition to, or in place of, electrical stimulation, other methods to confirm placement can also be used, such as measuring impedance or using imaging technologies, such as fluoroscopy. The use of an apparatus 102 with a shaft 114 whose distal end is sharp or pointed allows apparatus 102 to be inserted without the need to first insert a separate introducer tube or needle thus further reducing the likelihood of positional shifting of apparatus 102. However, the use of an introducer is also envisioned.

After optionally administering the treatment composition, a high frequency, for example RF, electrical current may be applied to target area 120 through conductive region 112. Return dispersive electrode 108 is provided to create a closed circuit when apparatus 102 is electrically operated in contact with body 104. Notably, since fluid delivery mechanism 110 is still connected to apparatus 102 during energy delivery, further delivery of treatment composition coincident with the delivery of energy is possible. During treatment, temperature sensor feedback may be used to automatically control the RF energy delivered to body tissue 104 to help ensure safe operation of apparatus 102. For example, if the body tissue temperature increases rapidly while applying RF energy as measured by the temperature sensor feedback mechanism, RF energy delivery to body tissue 104 may be suspended or reduced to provide a controlled ramp to the desired set temperature. In this manner, the user does not blindly apply RF energy to the body tissue, but is informed in real-time of the effects that RF energy delivery has on tissue temperature.

In some embodiments, as has been previously described, flexible tube 124 may provide the mechanical slack required to ensure that fluid delivery does not introduce added force to apparatus 102. Other treatment tools, depending on the procedure, may also be flexibly connected to apparatus 102. Apparatus 102 may therefore be provided with pre-formed connectors for these treatment tools that are flexibly coupled to apparatus 102.

In some embodiments of the disclosure, in order to facilitate precise placement of conductive region 112, conductive region 112 is made distinguishable from the rest of apparatus 102 when viewed under x-ray fluoroscopy (or other radiographic imaging modalities) by providing a radiopaque marking at or adjacent the proximal end of conductive region 112 or at another location of shaft 114. Alternatively, another form of marking, including, but not limited to, a magnetic or paramagnetic marking, may be provided, in order to visualize conductive region 112 using various medical imaging modalities such as MRI, ultrasound and CT.

Figure 3:
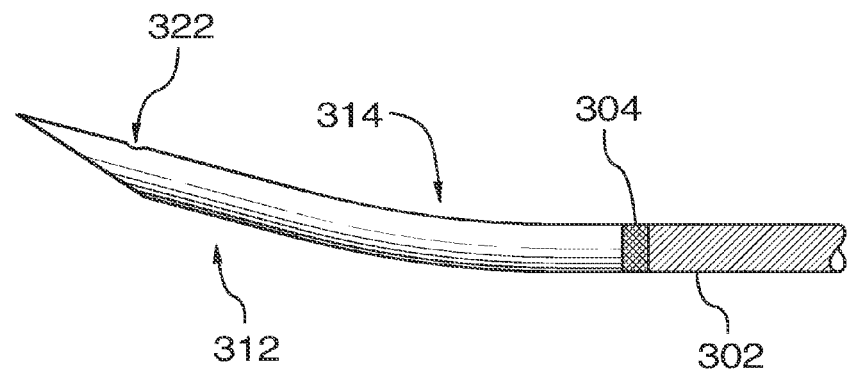
FIG. 3 is a side elevation view of a distal region of an alternate electrosurgical apparatus in accordance with an alternative embodiment of the disclosure.

Another embodiment of a shaft 114 of a surgical apparatus aspect of the disclosure can be seen in FIG. 3. This embodiment of shaft 114 comprises a textured surface 302, a radiopaque marker 304, and a curved conductive region 312. Conductive region 312 defines an aperture 322 on the inside of curve 314 and a temperature sensor (not shown) at or proximate the distal end of conductive region 312. Textured surface 302 allows for strong adhesion of insulating coating (not shown) to shaft 114 of apparatus 102 by increasing the shaft surface area. Radiopaque marker 304 provides visibility of the junction between curved conductive region 312 and insulated (or otherwise non-conductive) portions of shaft 114 under radiographic imaging. For example, radiopaque marker 304 may be placed so as to define the distal end point of the insulating coating (not shown) and the proximal start point of conductive region 312. It should be understood by those skilled in the art that radiopaque marker 304 may include any arrangement or length of radiopaque marking(s) along shaft 114 of apparatus 102. Other arrangements of radiopaque markings may include a series of equidistant markers to indicate insertion depth or may include radiopaque marking along the length of shaft 114, optionally proximal to conductive region 312. Equidistant depth markings may not necessarily be radiopaque, but may be colored to contrast with shaft 114 and to be visible to the user. Curved conductive region 312 provides added maneuverability of shaft 114 while it is advanced through body tissue 104. Having aperture 322 oriented on the inside of curve 314 prevents the edge of aperture 322 from cutting body tissue as shaft 114 is advanced through body tissue 104. However, aperture 322 may be positioned at various locations of shaft 114 and the disclosure is not limited in this regard. Furthermore, it should be noted that alternate embodiments of the present disclosure may comprise an apparatus having a curve without a textured surface or a textured surface without a curve. In addition, a curve may be present at other locations of shaft 114. Further embodiments of the present disclosure may comprise a shape altering mechanism (or a shape actuator) in order to steer apparatus 102 within a patient's body. The shape actuator may include, but is not limited to, cables for a mechanical actuator, hydraulic or piezo-electric devices and solenoids.

Figure 4A:
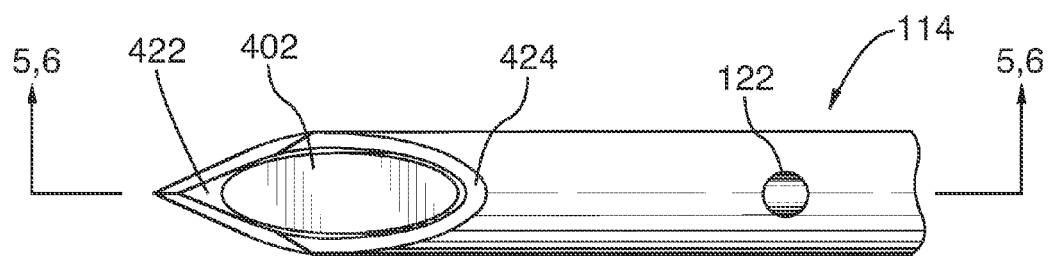
FIGS. 4A-4B are plan elevation views of two embodiments of a distal region of an electrosurgical apparatus in accordance with two embodiments of the disclosure comprising a stylet.
Figure 4B:
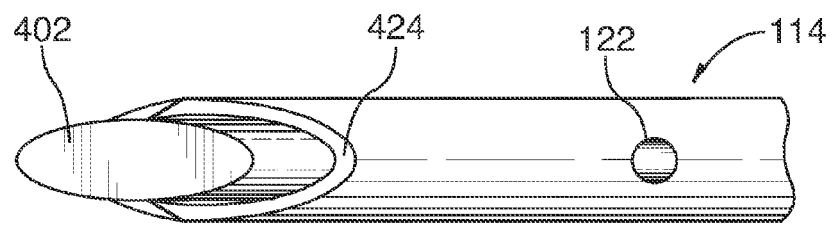
Figure 5A:
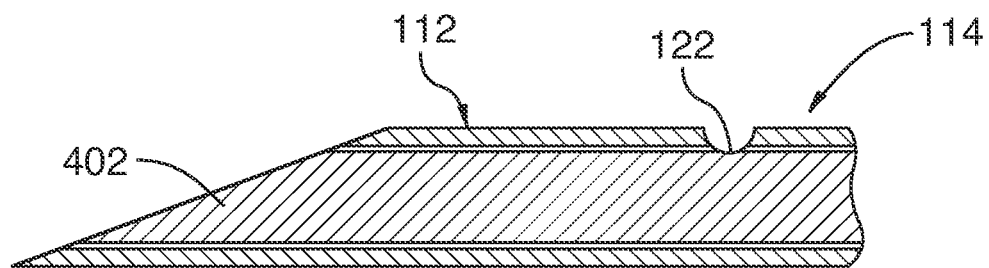
FIGS. 5A-5C are sectional side views through the shaft of various embodiments of the disclosure comprising a stylet.
Figure 5B:
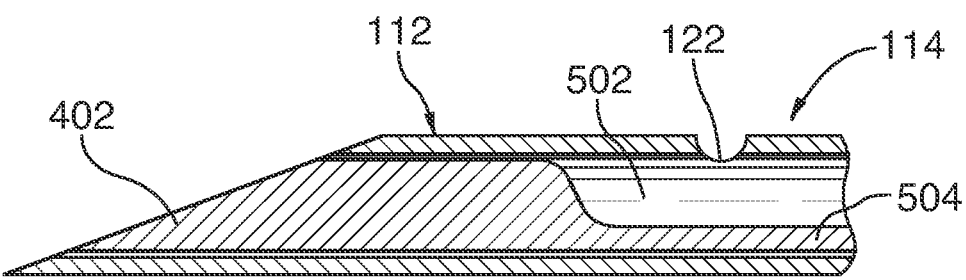
Figure 5C:
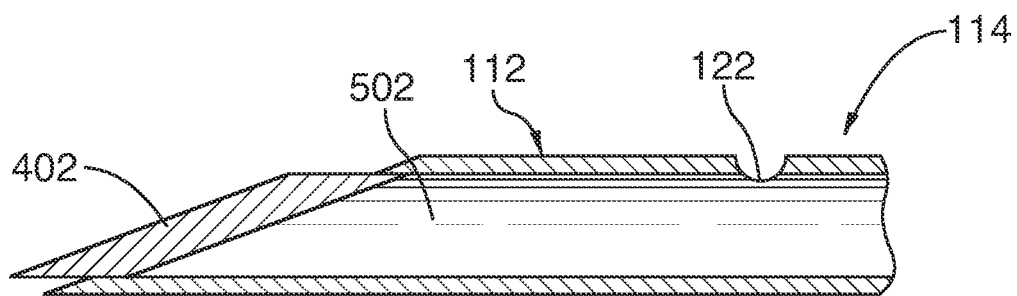

As has been described, shaft 114 may be sufficiently dimensioned so as to accommodate a stylet or obturating device. Enlarged top elevation views of two exemplary embodiments of the distal region of apparatus 102, comprising a stylet 402, are shown in FIG. 4. Referring first to FIG. 4A, shaft 114 defines a distal opening 422 at a distal boundary 424 thereof and the lumen of shaft 114 contains stylet 402, substantially occluding distal opening 422 of shaft 114; in such an embodiment, a distal end of stylet 402 has substantially the same shape as that of distal boundary 424 of shaft 114 and is flush with distal boundary 424. Stylet 402 serves to discourage tissue from entering the lumen of shaft 114. FIG. 4B shows an alternate embodiment whereby stylet 402 protrudes from the distal end 424 of shaft 114. In further embodiments, only a portion of stylet 402 may protrude from distal boundary 424 of shaft 114. Alternatively, stylet 402 may not completely occlude distal opening 422. For example, at least a portion of stylet 402 may be recessed inwards from the distal boundary 424 of shaft 114. FIGS. 5A-C show various embodiments of the disposition of stylet 402 within shaft 114. In one embodiment, shown in FIG. 5A, stylet 402 may substantially fill the lumen defined by shaft 114. Alternatively, stylet 402 may only partially fill the lumen, leaving a luminal space 502 between the exterior surface of a stylet shaft 504 and the interior surface of shaft 114, as shown in FIG. 5B. Although FIG. 5B shows stylet shaft 504 extending along one side of shaft 114, it should be understood that stylet shaft 504 can be located at any position within shaft 114, for example near the center of shaft 114. In a further embodiment, shown in FIG. 5C, stylet 402 is in the form of a cap or plug that occludes at least a portion of distal boundary 424 of shaft 114 and that may be affixed to the distal end of shaft 114, for example by welding, but which does not extend through the length of shaft 114.

Stylet 402 may be removable from shaft 114, or may be affixed to shaft 114, for example by welding, at one or more locations. Where stylet 402 is positioned such that a luminal space 502 is present, welding stylet 402 to shaft 114 can serve to reduce the radial and axial movement of stylet 402 within shaft 114.

In one specific embodiment, stylet 402 may be made from a conductive material, such as stainless steel. In this embodiment, stylet 402 may be connected to shaft 114 or may be otherwise electrically coupled to shaft 114 and may thus be operable to deliver energy to a patient's body. Alternatively, stylet 402 may be independently connected to power source control unit 106. If stylet 402 is conductive and is coupled to shaft 114 or power source control unit 106, conductive region 112 may be defined as comprising the portions of shaft 114 and stylet 402 that deliver energy to target tissue area 120.

Figure 6A:
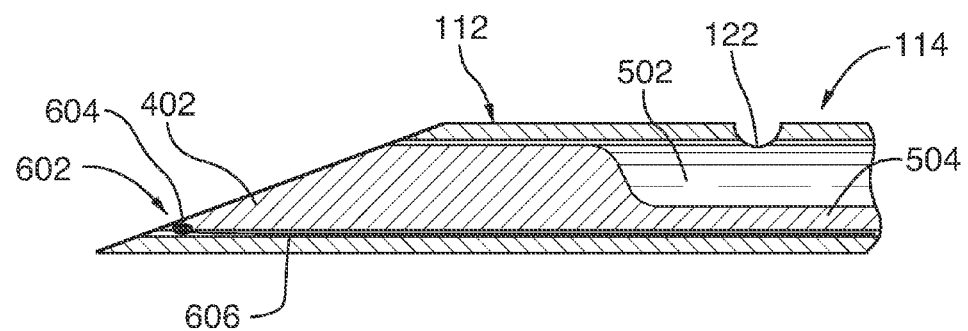
Figure 6B:
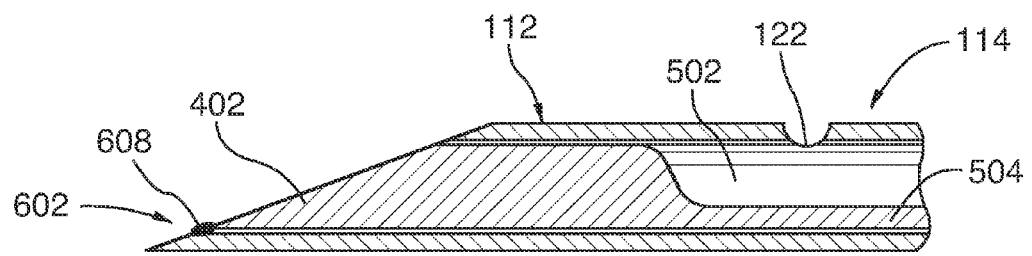

FIGS. 6A and 6B shows two exemplary embodiments of a distal region of apparatus 102 comprising a temperature sensor 602, aperture 122 and conductive region 112 (including the conductive regions of shaft 114 and stylet 402 where applicable, as described above). Temperature sensor 602 may be welded to the distal end of conductive region 112, for example, either to shaft 114 or to stylet 402. In some embodiments, as has been mentioned, temperature sensor 602 is a thermocouple, which may optionally include one or more thermocouple wires 606 running in the lumen of shaft 114 and insulated from conductive shaft 114 and from any other conductive structure electrically coupled to shaft 114 or to power source control unit 106. Insulation may include either insulation on the luminal surface (the surface facing the lumen through which the wire or wires run) of shaft 114 and other conductive structures, or insulation on the outer wall of the wire or wires.

The general use of a thermocouple to measure temperature is known in the art. However, in one embodiment, conductive region 112 may be a component of thermocouple 602, as follows: the distal end of a thermocouple wire, made of a material that differs from the material of conductive region 112, may be minimally stripped of insulation; temperature sensor 602 may then be formed by welding the distal end of the thermocouple wire to conductive region 112 of shaft 114 to create a thermocouple. Thus, shaft 114 and conductive region 112 may serve dual purposes, being utilized for energy delivery as well as forming a portion of temperature sensor 602. In other embodiments, rather than forming a temperature sensor using conductive region 112, as described above, a separate, self-contained temperature sensor may be attached to conductive region 112. In any embodiment of the present disclosure, temperature sensor 602 need not comprise a thermocouple, and may comprise a thermistor, thermometer, optical temperature sensor or other temperature sensor. Furthermore, apparatus 102 may contain any number of temperature sensors, which may be positioned at a variety of locations along the side of the apparatus, not only at or near conductive region 112, and which may protrude from, be flush with, or be recessed into the surface of conductive shaft 114. In embodiments comprising a stylet 402 and a thermocouple 602, stylet 402 may be a component of thermocouple 602. In one such embodiment, illustrated in FIG. 6A, thermocouple junction 604 is formed by the welding of a wire 606 to stylet 402. For example, if stylet 402 was made from stainless steel, a constantan (or any other wire made of a conductive material other than stainless steel) wire 606 might be used. In such an embodiment, stylet 402 may be welded or otherwise connected to shaft 114 at some other location of shaft 114. In another embodiment, shown in FIG. 6B, stylet 402 may be made of one metal (for example, constantan) and shaft 114 may be made of a dissimilar metal (for example, stainless steel); stylet 402 may then be welded to shaft 114 in order to create a thermocouple junction 608. In embodiments wherein the stylet 402 is a component of thermocouple 602, stylet 402 may also be used to deliver energy from an energy source, as described hereinabove. Thus, stylet 402 may be used for a plurality of functions including, but not limited to, delivering energy and measuring temperature, thereby further reducing the bulkiness of the electrosurgical apparatus and further reducing the costs associated with manufacturing the apparatus. In such an embodiment, a constantan wire (not shown in FIG. 6B) may extend from a proximal end of stylet shaft 504 in order to provide temperature information to power source control unit 106. In any embodiments including a thermocouple wire, rather than being loose within the apparatus, the wire may be secured along at least a portion of the longitudinal length of the apparatus, in order to prevent the wire from being damaged during manipulation of the apparatus. For example, the wire may be secured to a proximal portion of the stylet using various means of attachment including, but not limited to, heat shrink and adhesive. Although thermocouple junction 608 is shown at a tip of shaft 114, other embodiments may have thermocouple junction 608 at an alternate location along shaft 114. As has already been mentioned, more than one temperature sensor may be present on apparatus 102 and any temperature sensor may be a thermocouple, thermistor or other temperature sensing means.

In an embodiment, the distal end of shaft 114 is sharpened in order to allow apparatus 102 to be inserted into body 104 without the use of an introducer tube or needle. Alternatively, in another embodiment, shaft 114 may not be sharpened, but stylet 402 may be sharpened or pointed and may protrude from shaft 114 in order achieve the same results as when shaft 114 is itself sharpened. As noted earlier, the circumferential edge of aperture 122, on the outer surface of shaft 114, is optionally smooth to prevent cutting of body tissue 104 while apparatus 102 is advanced therethrough. In some embodiments, stylet 402 may not completely occlude shaft 114, allowing treatment composition to exit a distal end of shaft 114 if it is in communication with fluid delivery mechanism 110. Thus, the term "aperture" as used herein is meant to include any opening in the body of shaft 114 and is not limited to a lateral aperture 122.

While the term stylet is used to refer to structure 402 as shown in the various Figures, this term is not intended to be exclusive, and is meant to include any obturator, trocar or other structure which, in embodiments with an open distal end, at least partially obstructs the distal end of shaft 114, in order to, for example, prevent the passage of tissue into shaft 114. The incorporation of a stylet into an apparatus of the present disclosure may be beneficial in that it may facilitate the incorporation of a temperature sensor 602 into apparatus 102 and make the process of manufacturing apparatus 102 more efficient.

FIGS. 6C to 6G show embodiments of a distal part of conductive region 112 of elongated shaft 114 including a lumen 60 that ends at the distal end of elongated shaft 114 at distal opening 422. A stylet 62 is shown inserted in lumen 60. These illustrated embodiments show only a single lumen but it is possible to have more than one lumen. The different embodiments of electrosurgical apparatus 102 can have stylet 62 being either affixed to the inside of shaft 114 or removable therefrom.

An elongated member 52 is provided extending through lumen 60 and stylet 62. While the illustrated examples show elongated member 52 being hollow, different structural configurations of elongated member 52 are possible, for example, being solid. Other features of the embodiments of FIGS. 6C to 6G that can vary include, for example, the thickness and position of elongated member 52, the dimensions of lumens of shaft 114 and the size and angle of the distal end of elongated shaft 114 and the angle of the distal end of stylet 62.

A temperature sensor that can possibly be a thermocouple, thermistor, thermometer, optical temperature sensor or another type of temperature sensor, is a component of distal end 53 of elongated member 52. It is also possible that the sensor be a thermocouple for measuring impedance. The illustrated sensor 54 of FIGS. 6C to 6G can possibly be a thermocouple junction 54 formed by wire 50 being joined to elongated member 52. Wire 50 can be located inside or outside of elongated member 52. It is possible to for the embodiments of FIGS. 6C to 6G to have the elongated member be comprised of a hypotube 52, possibly stainless steel, that encloses and supports an insulated constantan wire 50 (or any other wire made of an insulated conductive material other than stainless steel) with the hypotube and constantan wire being welded together at the distal end of the hypotube to form thermocouple junction 54. Other variations are possible, such as the inside of the tube being insulated. Having the wire located inside of a tube can protect the wire, in particular when a stylet is removed or inserted. The temperature sensor can allow for monitoring of temperature throughout a surgical procedure and can be used to control the delivery of the high frequency energy to help ensure safe operation of apparatus 102. Stylet 62 can function as both a probe and a traditional stylet, eliminating the need for a traditional stylet when inserting a surgical instrument. The stylet can be electrically coupled to an electrical connector for connecting the stylet to an energy source to deliver energy, possibly for RF ablation. As stylet 62 may be used for a plurality of functions, it is possible to reduce the number of different electrosurgical apparatus and the associated costs. Surgical stylet 62 described herein reduces or eliminates the need for removal and reinsertion of both a stylet and a probe during a procedure.

It should be noted that that in the description of FIGS. 6C to 6G the terms "obturate" and "occlude" both have the same dictionary meanings of "stop up" and "close" and in this disclosure are both intended to describe the same general function of occluding distal opening 422 to prevent coring during insertion of shaft 114. The terms "occlude" and "obturate" are not intended to be limited to describing completely closing the distal opening such as to prevent fluid flow but rather to describe substantially occluding the opening enough to prevent coring while possibly/optionally still allowing fluid through an non-occluded potion of the distal opening. The term "occlude" is used most often throughout the description ad is intended for use when describing the "stopping up" function of the stylet components, for example, distal surface 55 of elongated member 52, laminate exterior of lamina 70 and distal face 58 of occluding component 56 and sometimes for the stylet. In certain case, for the sake clarity, the term "obturated portion" is used to describe the portion of the distal opening that is obturated or occluded by the entire stylet and is related to the term "obturate" which is sometimes used to describe the "stopping up" function of the entire stylet.

In FIG. 6C, elongated member 52 has distal surface 55 [that can function to occlude a portion of distal opening 422]. The stylet of FIG. 6C comprises an elongated member 52 including a distal end 53 having an occluding component 56 attached thereto. Elongated member 52 can be a hypotube thermocouple. Other possible terms for the occluding component optionally include hat, cap, sleeve and stopper. Occluding component 56 functions towards occluding at least a portion of distal opening 422 such that stylet 62 will prevent coring, gouging or tissue accumulation when inserting shaft 114 of apparatus 102 into a patient.

In the embodiment of the disclosure illustrated in FIG. 6C, occluding component 56 defines a beveled distal face 58 that is shown as being substantially flat. There can also be variations of the angle, curvature and shape of distal face 58. Occluding component 56 can optionally be comprised of a plastic, metal, ceramic or some other bio-compatible material.

Relative to distal face 58 of occluding component 56, distal end 53 of elongated member 52 can be recessed, flush or protruding. In the illustrated embodiment of FIG. 6C, distal end 53 of elongated member 52 extends beyond distal face 58 of occluding component 56 at distal surface 55.

Various configurations of an inserted stylet 62 relative to the distal end of shaft 114 are possible, for example, stylet 62 being recessed, flush with or extending beyond the distal end of shaft 114. Whether the distal end of stylet 62 is recessed, flush or protruding, a functioning stylet 62 can occlude enough of distal opening 422 and withstand insertion forces to prevent coring, including embodiments in which elongated member 52 is a hypotube thermocouple. The distal end of stylet 62 can comprise distal face 58 of occluding component 56, distal surface 55 of elongated member 52 and other possible parts. Stylet 62 can be removed for embodiments not having it fixed inside shaft 114.

The occluding component 56 can possibly be a plastic that is overmolded to bond onto elongated distal end 53 to form a plastic cap, possibly a plastic beveled cap. The bonding surface of the elongated member can be roughened in preparation for overmolding to improve bonding. The plastic can be of different types of plastic and could possibly be a hard plastic such as pvc or a soft plastic such as Santoprene™, and could further possibly be an echogenic or radiopaque material. It is also possible that a radiopaque marker (not shown) could extend the length of occluding component 56.

FIG. 6C shows distal end 53 of elongated member 52 centered relative to occluding component 56 but it is possible for distal end 53 to be off center relative to occluding component 56 such that the elongated member of an inserted stylet will be positioned off center of shaft 114.

Figure 6G:
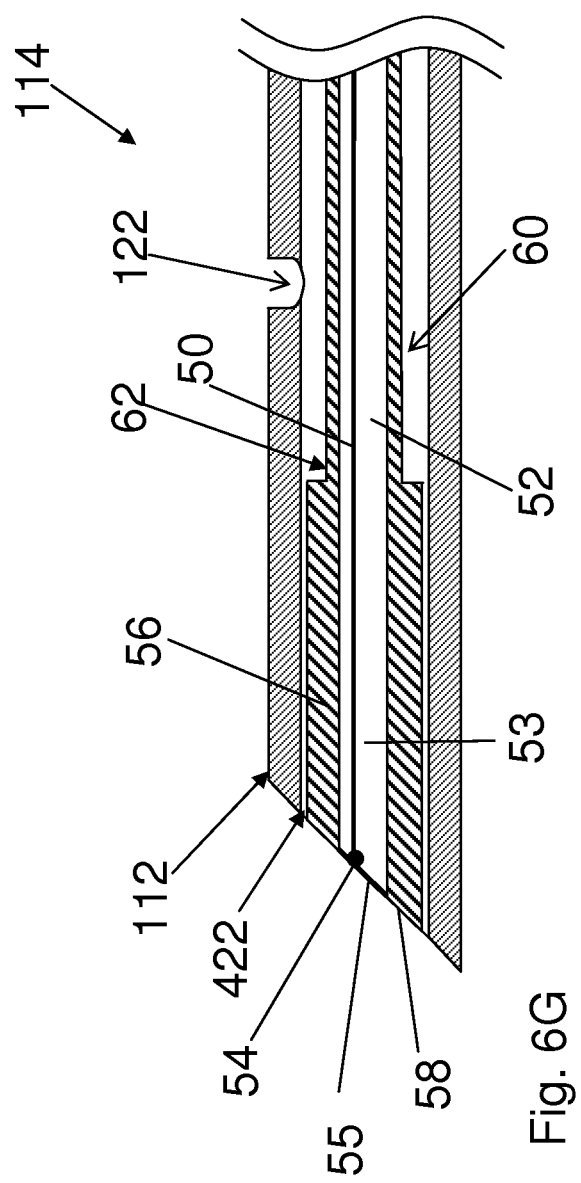

As would be understood by one skilled in the art, many of the variations related to the embodiment of FIG. 6C could be relevant to the embodiments of FIGS. 6F and 6G, which also have occluding components.

FIGS. 6D and 6E show possible embodiments that lack occluding component 56. The diameter of distal opening 422 is sized so that distal end 53 of elongate member 52, including distal surface 55, substantially occludes at least a majority of distal opening 422. Shoulder 84 (FIG. 6D) and shoulder 88 (FIG. 6E) partially obturate lumen 60 and support/position elongated member 52. Elongated member 52 can comprise a hypotube thermocouple 52. The diameter of distal opening 422 is less than the diameter of lumen 60 at a proximal region of elongated shaft 114. In the illustrated embodiment of FIG. 6E the diameter of lumen 60 gradually decreases towards the distal end opening while in the embodiment of FIG. 6D, the diameter of the lumen decreases at a substantially discrete location along elongated shaft 114.

FIG. 6F shows a lamina 70 located on distal face 58 of occluding component 56. It is possible for a lamina 70 to be a distinct part fixed to or formed upon distal face 58, or alternatively lamina 70 and occluding component 56 could be comprised of one integral component. In embodiment of FIG. 6F, lamina 70 includes lamina exterior 72.

In one possible embodiment, occluding component 56 is comprised of a metal with a metal lamina 70 fixed to or formed on the end of occluding component 56. More specifically, occluding component 56 can comprise a metal tube with a beveled distal face 58 and with the metal tube having an inner diameter that corresponds to the outer diameter of elongated member 52 (possibly a hypotube thermocouple). Occluding component 56 can be attached to a hypotube thermocouple 52, possibly by welding, such as laser welding. The metal tube can optionally be described as a sleeve or cap. As a metal layer lamina 70 would be a heat conductor, it could cooperatively function with heat sensor 54 to supply temperature data.

Lamina 70 can vary in size and shape and in some embodiments could possibly not cover all of the distal face of stylet 62. Whatever the configuration of lamina 70, the distal end of stylet 62 of the embodiment of FIG. 6F can obturate, at least in part, distal opening 422.

As elongate member 52 (possibly a hypotube thermocouple) does not completely fill the portion of lumen 60 that it extends, it is possible that fluid may be injected through lumen 60 with the fluid exiting through aperture the 122 and/or the non-obturated part of distal opening 422.

It is also possible the illustrated embodiments of FIG. 6F could include occluding component 56 and/or lamina 70 being comprised of radiopaque materials, whether the parts are distinct or unitary, such as to be viewable under fluoroscopy. It is also possible that a radiopaque marker or markers (not shown) could be attached to occluding component 56 and/or lamina 70.

In the example of FIG. 6G, occluding component 56 and elongate member 52, including distal surface 55, are formed of a single unitary part. For illustrative purposes, the example of FIG. 6G portrays elongate member 52 as having sidewall 80 of sufficient thickness such that cross hatching can be used to indicate that the parts are made of the same material. This is for illustrative purposes only and should not be taken as limiting. The sidewall thickness of elongated member 52 of the various embodiments can vary, depending on the desired characteristics such as, for example, desired strength and flexibility. The embodiment of FIG. 6G could be realized, for example, by a hypotube with a larger diameter end (possibly having a different shape than in FIG. 6G) or alternatively the embodiment of FIG. 6G could be realized by an occluding component with a hollow elongated extension. The possible example of FIG. 6G could possibly be described as a hollow stylet.

As elongate member 52 (possibly a hypotube thermocouple) of FIG. 6G leaves part of lumen 60 un-occluded, it is possible that fluid may be injected through lumen 60 with the fluid exiting through aperture the 122 and/or the non-obturated part of distal opening 422.

Distal end 53 of elongated member 52 could have variations of shape for all of the embodiments of FIGS. 6C to 6G, including, for example, a rounded tip (FIGS. 6C to 6F) or a beveled tip (FIG. 6G).

It will be understood by those skilled in the art that other stylet embodiments are possible. For example, though not shown in the drawings, a stylet could have a transmitter for transmitting data from a sensor.

It is another aspect of the disclosure to provide a stylet by itself for fitting into a corresponding lumen of an elongated shaft of an electrosurgical apparatus for treating tissue. Different embodiments of such a stylet are possible, including all of those previously described.

Figure 7A:
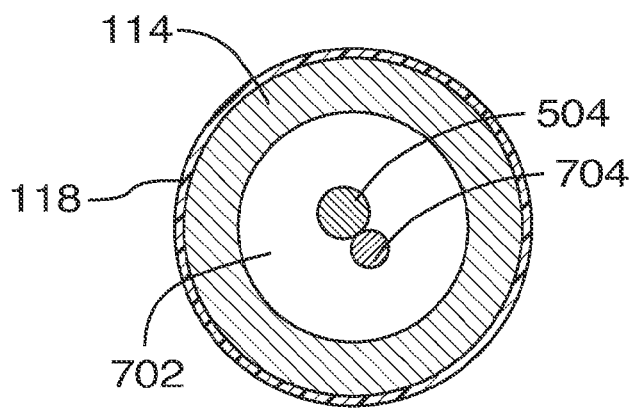
FIGS. 7A-7C are sectional front views through the shafts of various embodiments of the disclosure comprising an electrosurgical apparatus.
Figure 7B:
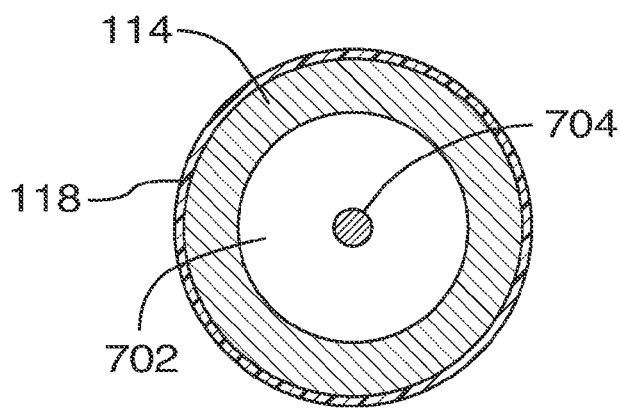
Figure 7C:
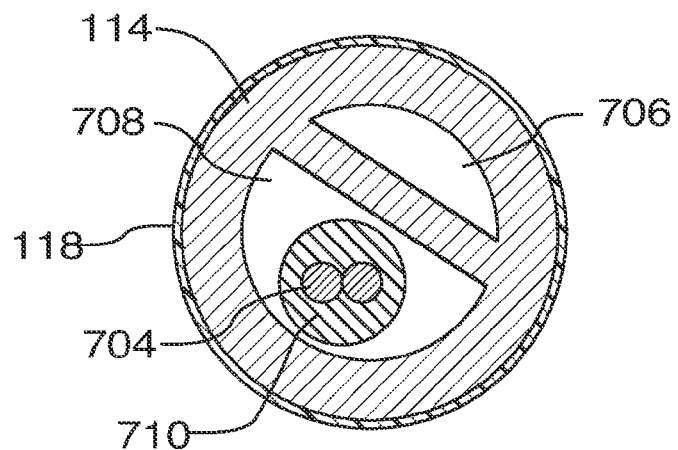

Referring now to FIGS. 7A-C, sectional side views of a portion of conductive shaft 114 comprising insulating coating 118, as illustrated in FIG. 1, are shown. In the embodiment shown in FIG. 7A, shaft 114 defines a lumen 702, as has been described. Stylet shaft 504 and temperature measurement wire or wires 704 run through lumen 702. In one embodiment, the present disclosure comprises a single wire 704 housed in lumen 702 of conductive shaft 114, and welded to a dissimilar metal to form temperature sensor 602. As mentioned above, the welding of wire 704 to a dissimilar metal may entail welding to shaft 114 or to stylet 402. Alternatively, temperature wires 704 may comprise two or more wire components of a temperature sensor associated with apparatus 102. Although FIGS. 7A and 7B show wire 704 and stylet shaft 504 (in FIG. 7A; in the embodiment shown in FIG. 7B, stylet shaft 504 is not present within lumen 702) located substantially in the center of lumen 702 defined by shaft 114, it should be clear that this is not intended to be limiting and that wire or wires 704 and/or stylet shaft 504 may be located at various positions within lumen 702. Another embodiment of a shaft 114 of apparatus 102 is shown in FIG. 7C. This embodiment comprises a first lumen 706 and a second lumen 708. Wiring 704 for temperature sensor 602 and conductive region 112 (in embodiments comprising such wiring) of apparatus 102 run through second lumen 708, optionally contained within an insulating covering 710. First lumen 706 may be beneficially used as a passage for the injection of a treatment composition. The size of lumen 706 and lumen 708 and the number of lumens required may vary depending on the embodiment. Another embodiment (not shown) comprises a plurality of lumens, for example as shown in FIG. 7C, as well as a stylet housed within one of the lumens.

Figure 8:
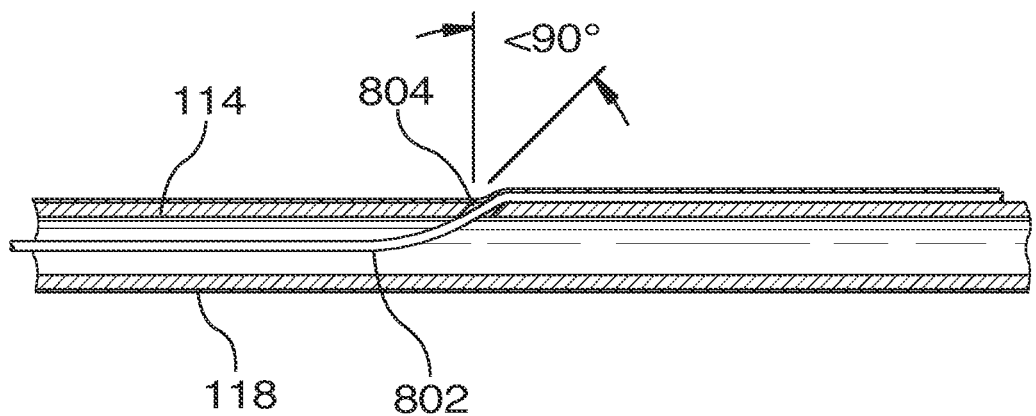
FIG. 8 is a sectional side view through the shaft of one embodiment of the disclosure comprising an electrosurgical apparatus.

Referring now to FIG. 8, a magnified sectional view of a portion of shaft 114, according to one embodiment, is shown. In this embodiment, thermocouple wiring 802 exits the lumen of conductive shaft 114 through a wiring aperture 804. Wiring aperture 804 is optionally angled less than 90° with respect to the axis of conductive shaft 114, as shown in FIG. 8, in order to minimize bending of wiring 802. Use of this angle provides additional strain relief and protects the insulation of thermocouple wiring 802 as it exits shaft 114, lies parallel to conductive shaft 114, and is covered by insulating coating 118. In alternate embodiments, any wires may exit shaft 114 at any angle. In yet further embodiments, all wires associated with apparatus 102 may remain within shaft 114 until a proximal end of shaft 114 is reached.

Though not shown, another embodiment of a surgical apparatus aspect of this disclosure provides an apparatus comprising a shaft 114 and a conductive region 112 constructed from separate components. Shaft 114 could be made of a conductive material and then coated with an insulating material as in the embodiment shown in FIG. 1 or could be made from a non-conductive material such as, but not restricted to, polyetheretherketone (PEEK). Conductive region 112 is made of a conductive material and attached to non-conductive shaft 114. There are various methods in which conductive region 112 could be attached to non-conductive shaft 114 including, but not limited to, chemical bonding, press fits and screw fits. The wiring for the temperature sensor (in embodiments comprising a temperature sensor) and the conductive region (i.e. the wire or other means of transmitting electrical energy from a power source to the conductive region) may extend through and along a lumen of shaft 114 and connect to conductive region 112. Alternately, in any of the embodiments of the present disclosure, the wiring for one or more of the temperature sensor and conductive region 112 may be extruded in the walls of shaft 114 such that the lumen could be used to deliver treatment composition but may not be required to house wiring.

Conductive region 112 can therefore serve multiple purposes. Conductive region 112 can be the site of passage for electric current to the surrounding tissue. It can also be the site for the release of a treatment composition. Finally, conductive region 112 can also house one or more temperature sensors. Various tip geometries, such as a bevel on the end of the conductive region with a bottom hole and a mid-bevel temperature sensor are also contemplated embodiments (not shown). It should be understood that various other tip shapes and sizes; aperture sizes and placements, and temperature sensor placements are also considered to be viable options.

The embodiments of the disclosure described above are intended to be exemplary only. For example, although the disclosure has been described primarily utilizing RF or other high-frequency energy, other forms of energy may be used as well, including but not limited to thermal energy. The scope of the disclosure is therefore intended to be limited solely by the scope of the appended claims.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure.

We claim:

1. An electrosurgical apparatus for treating tissue, comprising:
an elongated shaft including a proximal region and a distal region comprising a conductive region, the elongated shaft defining a lumen that extends from the proximal region to the distal region; and
a stylet located within said lumen, said stylet comprising an elongated member having a proximal end and a distal end and a separate occluding component, said distal end of the elongated member comprising a sensor, the occluding component comprising an overall length extending from a first end to a second end and a constant outer diameter extending from the first end to the second end, the second end defining a distal face, the occluding component substantially surrounding the distal end of the elongated member and fixed within said lumen so as to obturate at least a portion of an opening defined by a distal and of said elongated shaft to define an obturated portion,
wherein the occluding component extends from the distal end of the elongated member and ends before the proximal end of the elongated member such that the proximal region of the shaft is unobstructed by the occluding component, the distal end of the elongated member extending beyond the distal face of the occluding component such that sensor is distal to and spaced apart from the distal face of the occluding component, and wherein the elongated shaft and the stylet are configured to allow passage of fluid through said lumen while said stylet is located within said lumen.

2. The electrosurgical apparatus of claim 1, wherein the sensor comprises a thermocouple junction.

3. The electrosurgical apparatus of claim 1, wherein said distal face of the occluding component defines a beveled distal face.

4. The electrosurgical apparatus of claim 3, wherein said occluding component comprises a metal; and
wherein said stylet further comprises a metallic lamina disposed upon at least a portion of said beveled distal face.

5. The electrosurgical apparatus of claim 1, wherein a wall of said elongated shaft defines one or more apertures in communication with said lumen.

6. The electrosurgical apparatus of claim 1, wherein said apparatus further comprises a radiopaque marker extending the length of said occluding component.

7. The electrosurgical apparatus of claim 1, wherein said occluding component is comprised substantially of radiopaque material.

* * * * *